United States Patent [19]

Nowak

[11] Patent Number: 4,858,128

[45] Date of Patent: Aug. 15, 1989

[54] VIEW-TO-VIEW IMAGE CORRECTION FOR OBJECT MOTION

[75] Inventor: David J. Nowak, Greendale, Wis.

[73] Assignee: General Electric Company

[21] Appl. No.: 895,316

[22] Filed: Aug. 11, 1986

[51] Int. Cl.$^4$ .......................... G06K 9/40; G06F 15/42
[52] U.S. Cl. .................................. 364/413.13; 382/6; 382/44
[58] Field of Search ...................... 364/414; 382/6, 54, 382/33, 42; 358/111; 378/901

[56] References Cited

U.S. PATENT DOCUMENTS

| | | | |
|---|---|---|---|
| 4,510,617 | 4/1985 | Mori | 382/33 |
| 4,580,219 | 4/1986 | Pelc et al. | 364/414 |
| 4,635,293 | 1/1987 | Watanabe | 382/6 |
| 4,641,352 | 2/1987 | Fenster et al. | 382/6 |
| 4,654,875 | 3/1987 | Atkins | 382/42 |
| 4,669,054 | 5/1987 | Schlunt et al. | 382/42 |
| 4,685,146 | 8/1987 | Fenster et al. | 364/414 |

Primary Examiner—Charles E. Atkinson
Assistant Examiner—Kim Thanh Tbui
Attorney, Agent, or Firm—Thomas R. Morrison

[57] ABSTRACT

An imaging system of a type producing a plurality of X-Y matrices representing projection views of an object for later reconstruction using parts of a plurality of the views employs correlation techniques for determining the amount of motion along X and Y axes. The detected motion may be removed by suitably shifting later data to align it with earlier data, or vice versa. In one embodiment, all brightness values parallel to the X axes of two views are summed to develop two one-dimensional arrays containing information about the brightness patterns in the Y direction. One of the two one-dimensional arrays is shifted, and the two one-dimensional arrays multiplied, pixel-by-pixel, and the products are summed to provide a measure of similarity between the brightness patterns in the one-dimensional arrays. Repeated shifts produce a correlation function the shift position of whose maximum is a good approximation of the amount of motion occurring between the two views. The detected motion may be used to alert the operator that the data is faulty or to permit automatic alignment of all data from a scan. An identical process may be performed along the Y axis to detect and correct motion along the X axis, in certain restricted cases.

10 Claims, 5 Drawing Sheets

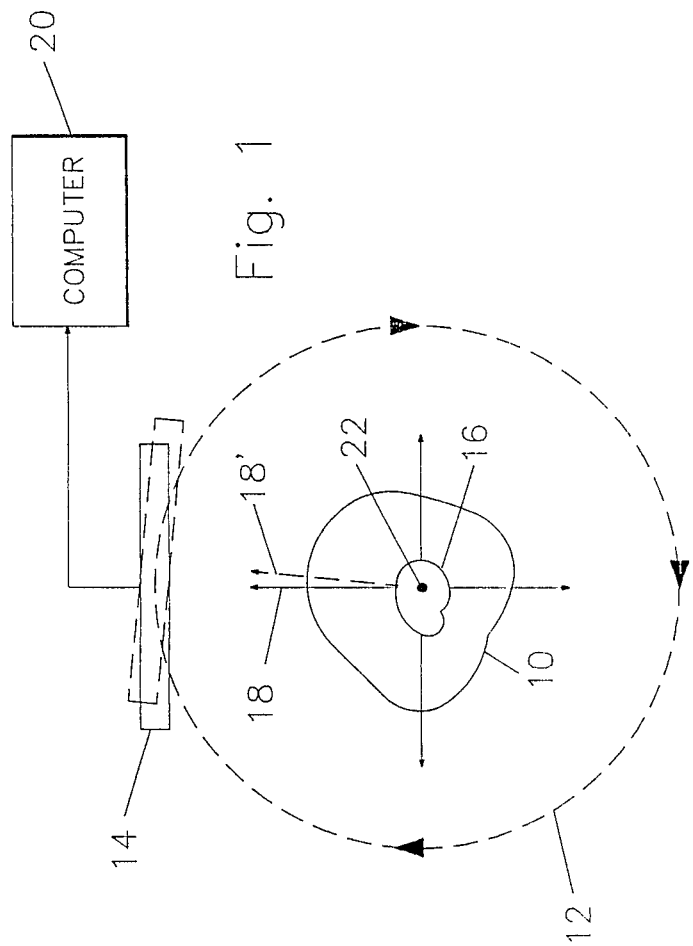

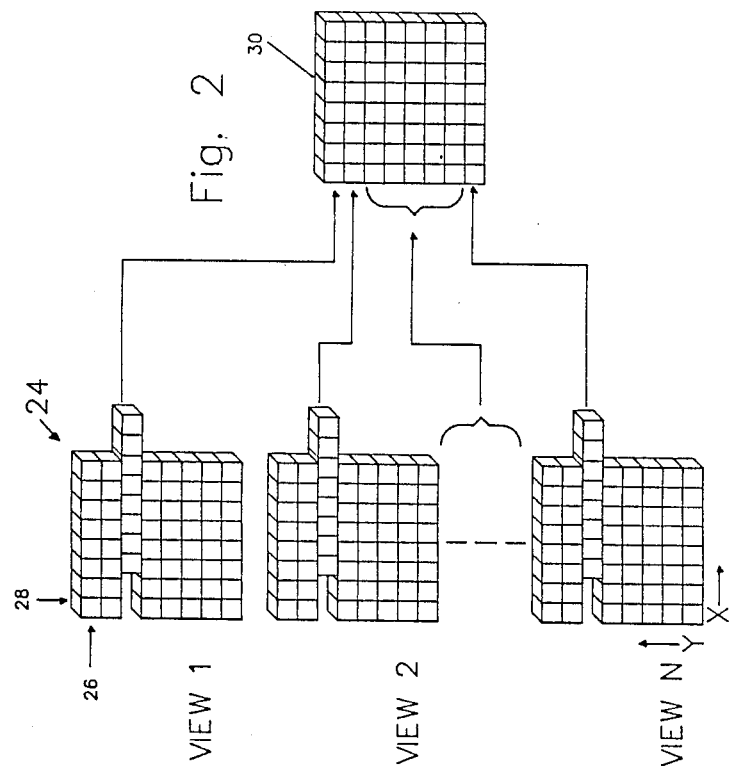

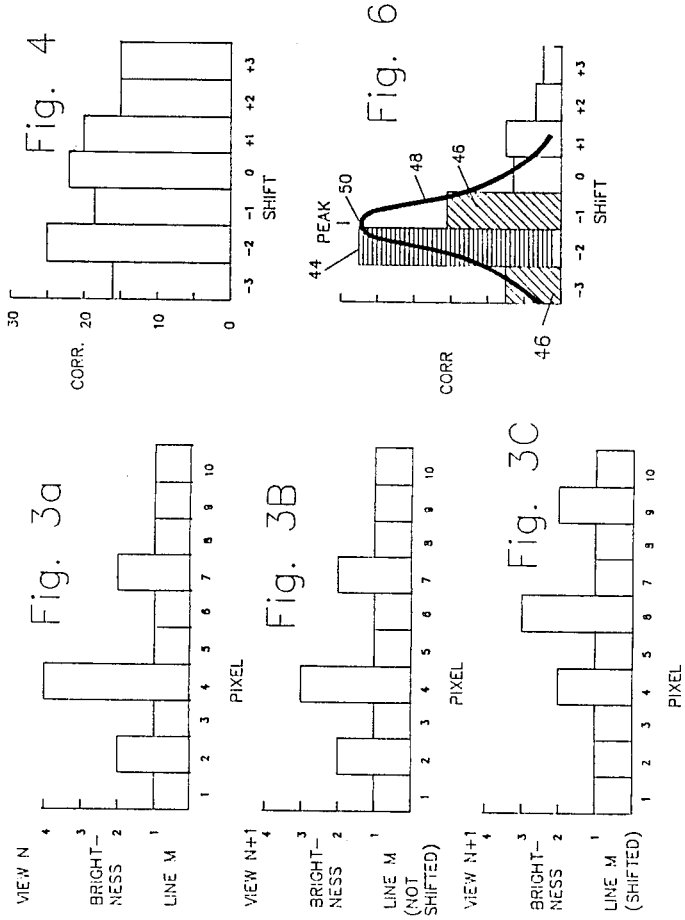

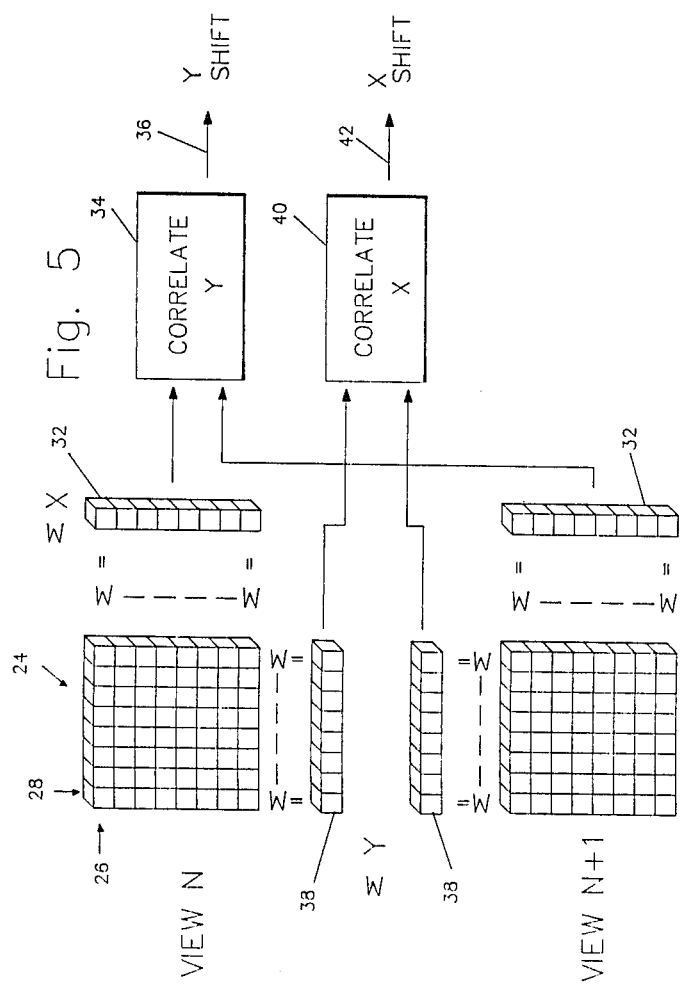

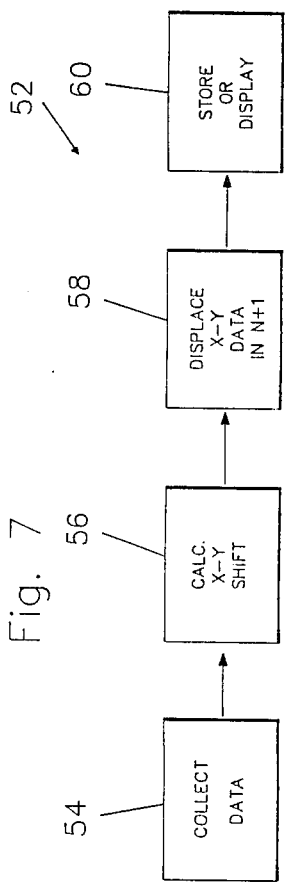

VIEW-TO-VIEW IMAGE CORRECTION FOR OBJECT MOTION

BACKGROUND OF THE INVENTION

The present invention relates to imaging and, more particularly, to detection of and correction for object motion in an imaging system where successive views from different positions are taken, each view representing a two-dimensional projection of the three-dimensional object.

Although the present invention may be employed in other types of imaging systems such as, for example, in X-ray computed tomography imaging, for concreteness of description the following disclosure is directed toward the invention in the environment of an emission tomographic system.

One type of emission tomographic system of interest is the single photon emission computed tomography (SPECT) system in which a low-level gamma ray emitter is injected into the body of a patient. The gamma ray emitter is conventionally of a type which preferentially travels to an organ whose image is to be produced. A large-area planar gamma ray detector detects gamma rays emitted from the body normal to its plane. This information is digitally stored as an image in an M by N array of elements called pixels. The values of M and N are conventionally equal to each other, and are commonly 64 or 128 units, or pixels, across the two dimensions of the image.

A SPECT system employs a plurality of views each taken by positioning a detector parallel to, and at an angle about a fixed axis. The angle is incremented in equal steps between views. The images thus captured are computer-processed to construct pictures of transaxial slices of the body. Computer processing utilizes portions of each succeeding view to reconstruct each transaxial slice. If the body being imaged changes position between successive views, the data from one view does not properly align with data from other views. As a consequence, images reconstructed from the data may be blurred, or contain artifacts of distortion in the imaging process which do not represent actual characteristics of the object being imaged.

In order to minimize the radiation dosage to which the patient is exposed, the injected gamma ray materials are of relatively low radioactivity. As a consequence, each view requires a substantial time such as, for example, about 40 seconds, to produce. If a total of 64 views on a 360-degree arc is desired, angularly spaced apart by about 5.6 degrees, then the entire imaging process takes about 40 minutes to complete. Blurring or distortion can take place when the body being imaged moves a distance on the order of one image pixel. A typical image pixel is about one-half centimeter square. Keeping a human body still to within one-half centimeter for 40 minutes is difficult, if not impossible. Thus, body motion and resultant image degradation are common.

The existence of body motion may be detected from the recorded data in a procedure, called cine mode, in which the entire set of views from the scan is displayed, one after the other, to create a simulated motion picture from which a human operator may observe whether an unacceptable amount of body motion took place during data collection. This technique is basically a quality control method for determining whether the collected data is usable. If the data is unusable, the alternatives are either to discount suitably the image data collected during image interpretation or to repeat the data collection. This technique does not provide means for correcting the data to remove motion-derived errors. In addition, the determination by the operator is at least partly subjective and thus open to operator error.

A further way of detecting body motion, called sinogram, is an image created by displaying the collected data which will later be used to construct a transaxial slice. The human operator is relied on to observe artifacts of body motion by visually detecting certain distortions in the sinogram image. As with cine mode, this is primarily a quality-control technique and does not permit correction of motion-derived errors. It similarly suffers from the need for subjective judgements by the operator.

A further technique such as disclosed, for example, in an article by J. S. Fleming entitled "A Technique for Motion Correction in Dynamic Scintigraphy", in the *European Journal of Nuclear Medicine* (1984) volume 9, pages 397–402, employs gamma ray emitting point sources applied to the body being imaged. The point sources are imaged along with the remainder of the body. Detected motion of the point sources may be used in a quality-control procedure and may provide sufficient data to apply manual correction factors to some of the affected data. This technique suffers the drawback that the presence of the point sources increases the radiation dosage to which the body is subjected. In addition, during full-circle data collection, the point sources are sometimes located at positions where they are blocked from the detector array by the body. Passage through the body may strongly attenuate the gamma radiation, thus degrading the ability to locate these point sources.

An automated technique for motion correction in an angiography system is disclosed in an article by Alain Venot and V. LeClerk entitled "Automated Correction of Patient Motion and Gray Values Prior to Subtraction in Digitized Angiography", in the *IEEE Transactions of Medical Imaging,* Volume M1-3, No. 4, December 1984, pages 179–186. This technique maximizes a deterministic sign change criterion with respect to two translational shifts and one constant value. When the shifts and constant value are such that the resultant noise-free image is close to zero, any noise in the image produces a signal shift, either positive or negative with respect to zero. At zero signal (noise only) the probability of the signal changing from plus to minus or vice versa is 0.5. This produces the maximum number of sign changes. Non-optimum values of the criterion place the resulting image farther from zero and superimposed noise has a reduced probability of producing a sign change. Thus, maximizing the sign change best compensates for patient motion.

A further article by Manbir Singh et al, entitled "A Digital Technique for Accurate Change Detection in Nuclear Medical Images—With Application to Myocardial Perfusion Studies Using Thallium-201", in *IEEE Transactions on Nuclear Science,* Volume NS-26, No. 251, February 1979, Pages 565–575, attempts registration of separate images taken at intervals of, for example, a week, wherein one of the images is taken under stress of exercise, and the other is taken unstressed. The method described in this paper requires user interaction, unlike the automatic techniques of the present invention.

OBJECTS AND SUMMARY OF THE INVENTION

Accordingly, it is an object of the invention to provide means for detecting body motion between successive views in a multi-view scanning system.

It is a further object of the invention to provide means and method for correcting image data to remove errors due to body motion during image data collection.

It is a still further object of the invention to provide an imaging system of a type producing a plurality of X-Y data matrices representing projection views of an object for subsequent tomographic reconstruction of axial slices of the object. The detected motion may be removed by suitably shifting later data to align it with earlier data, or vice versa. In one embodiment, all brightness values parallel to the X axes of two succeeding views are summed to develop two one-dimensional arrays containing information about the brightness pattern in the Y direction. One of the two one-dimensional arrays is shifted, and the two one-dimensional arrays multiplied, pixel-by-pixel, and the products are summed to provide a measure of similarity between the brightness patterns in the two one-dimensional arrays. Repeated shifts produce a correlation function related to the shift position at which they occur. The shift position producing a maximum in the correlation function is a good indication of the amount of motion occurring between the two views. The detected motion may be used to alert the operator that the data is faulty, or to permit automatic alignment of all data from a scan. An identical process may be performed by summing data parallel to the Y axis to detect and correct motion along the X axis, in certain restricted cases.

To detect shifts in the Y (axial) direction, a one-dimensional array of values is obtained by summing, for each value of Y, all pixel values in the X direction. This array is thus a sequence of values as a function of Y. For the case of ideal projection images, the values in this array are not a function of the view angle about the axis of rotation at which the data is acquired. Thus, the data in the Y array is the same, regardless of the view angle. In the case of emission tomography, where photon attenuation effects are significant, there are some differences in the Y array values as a function of the view angle. However, since the comparison is from one view image to the next, the detection method works reliably in this case as well.

To detect shifts in the X (tangential) direction, a one-dimensional array of values is obtained by summing, for each value of X, all pixel values in the Y direction. This array is thus a sequence of values as a function of X. For the case of ideal projection images, the values of this array generally change considerably as a function of view angle. Any single point in the object space produces a sinusoidal variation in the X direction as a function of the view angle. Complex images thus produce arrays of values which are not well correlated from one view to the next. Thus, generally, the described method cannot be used to detect object shifts in the X direction. I have found, however, that in the case of emission tomography, we often encounter the case where there is essentially one distributed source of activity. In this case, the correlation method does work in that it produces a value for the data shift from one view to the next. This shift is then compared to the expected sinusoidal displacement and the difference provides a measure of patient motion in the X direction.

Briefly stated, the present invention provides an imaging system of a type producing a plurality of X-Y matrices representing projection views of an object for later reconstruction using parts of a plurality of the views. The imaging system employs correlation techniques for determining the amount of motion along X an Y axes. The detected motion may be removed by suitably shifting later data to align it with earlier data, or vice versa. In one embodiment, all brightness values parallel to the X axes of two views are summed to develop two one-dimensional arrays containing information about the brightness patterns in the Y direction. One of the two one-dimensional arrays is shifted, and the two one-dimensional arrays multiplied, pixel-by-pixel, and the products are summed to provide a measure of similarity between the brightness patterns in the one-dimensional arrays. Repeated shifts produce a correlation function the shift position of whose maximum is a good approximation of the amount of motion occurring between the two views. The detected motion may be used to alert the operator that the data is faulty or to permit automatic alignment of all data from a scan. An identical process may be performed along the Y axis to detect and correct motion along the X axis, in certain restricted cases.

According to an embodiment of the invention, there is provided apparatus in an imaging system for correcting for inter-view motion, comprising: means for collecting first and second views of an object, the first and second views being taken from first and second different angles, each of the first and second views including at least one of M rows and N columns of image brightness data, means for comparing a first pattern of the image brightness data from the first view with a corresponding second pattern of the image brightness data from the second view to produce a coefficient containing information about a similarity therebetween, the means for comparing including means for applying a shift to one of the first and second patterns to a plurality of positions for producing a plurality of the coefficients, one at each of the plurality of positions, and means related to the plurality of coefficients for determining a value of the shift yielding a maximum of the similarity.

According to a feature of the invention, there is provided a method for correcting for inter-view motion in an imaging system, comprising: collecting first and second views of an object from first and second different angles respectively, each of the first and second views including at least one of M rows and N columns of image brightness data, comparing a first pattern of the image brightness data from the first view with a corresponding second pattern of the image brightness data from the second view to produce a coefficient containing information about a similarity therebetween, the step of comparing including applying a shift to one of the first and second patterns to a plurality of positions for producing a plurality of the coefficients, one at each of the plurality of positions, and determining, based on the plurality of coefficients, a value of the shift yielding a maximum of the similarity.

The above, and other objects, features and advantages of the present invention will become apparent from the following description read in conjunction with the accompanying drawings, in which like reference numerals designate the same elements.

BRIEF DESCRIPTION OF THE DRAWINGS

FIG. 1 is a simplified schematic diagram of an emission tomographic imaging system.

FIG. 2 is a schematic to which reference will be made in describing the manner in which a sinogram is constructed from portions of a plurality of views in the tomographic imaging system of FIG. 1.

FIGS. 3A-3C are simplified brightness curves to which reference will be made in explaining the correlation technique employed by the present invention.

FIG. 4 is the correlation function of the simplified brightness curves of FIGS. 3A-3C.

FIG. 5 is a schematic showing the correlation technique used in deriving the shift data in two succeeding views.

FIG. 6 is a set of curves showing how the correlation data derived in the apparatus of FIG. 5 may be analyzed to detect the shift to be applied to one of the images.

FIG. 7 is a functional block diagram of an imaging system employing an embodiment of the invention.

DETAILED DESCRIPTION OF THE PREFERRED EMBODIMENT

Referring to FIG. 1, a patient 10 is supported in a manner not shown in the center of a scanning path 12 traced out by a planar gamma ray detector 14. In preparation for scanning, patient 10 receives an injection of a radioactive substance having a close affinity for a body organ 16 about which image data is desired. The radioactive substance preferentially travels to body organ 16, thereby making body organ 16 a radioactive source, as indicated by rays 18. Although rays 18 radiate in all directions, planar gamma ray detector 14, as is conventional, responds only to those arriving substantially normal to its plane.

At one position, shown in solid line, planar gamma ray detector 14 senses an M by N rectangular array of radiation densities, each density representing a pixel of a planar image which may later be displayed on a suitable display device. M and N are conventionally equal to each other and are commonly 64 by 64 or 128 by 128 pixels. Each image is called a view. The collected pixel values of the view are transmitted to a computer 20 for storage and further processing, as will be explained.

After completing one view, planar gamma ray detector 14 is stepped around scanning path 12 in increments of a predetermined angle into a position indicated in dashed line, wherein it responds only to radiation arriving normal to its plane, indicated by a dashed ray 18'. The view in this position is likewise transmitted to computer 20. This process is completed by stepping planar gamma ray detector 14 at equal angles, over a 180-degree or a 360-degree arc about patient 10, taking a view at each position, and storing the data in computer 20. The angular steps may be, for example, about 5.6 degrees to produce 64 views over 360 degrees. It is conventional to take as many views over 360 degrees as there are pixels in one dimension of a view.

For purposes of later description, a Y axis is defined as an axis in planar gamma ray detector 14 parallel to an axis of rotation 22 of planar gamma ray detector 14. An X axis is defined as an axis in planar gamma ray detector 14 normal to the Y axis.

Referring now to FIG. 2, a view 24 is represented as a rectangular array of horizontal rows 26 and vertical columns 28. Although actual views 24 conventionally employ 64 by 64 or 128 by 128 pixels, reducing the number of pixels to an 8 by 8 array reduces complexity in the drawing without detracting from an understanding of the process being described. The third row 26 from subsequent views 24 form the remainder of the rows of sinogram image 30. The data in the sinogram is then used to reconstruct one transaxial slice image by employing conventional reconstruction techniques such as, for example, filtered back projection. As many transaxial slice images as there are rows 26 can be constructed in this way.

Since the data collection in succeeding views 24 is separated by a substantial time, motion of the body being imaged may displace data in one view 24 from that in neighboring views 24. As a consequence, a transaxial image created from the data in a sinogram may be blurred or have image artifacts due to the motion leading to missed or faulty diagnoses.

I have discovered that the image data in succeeding views can be used to determine the amount of motion taking place between them, and the information thus derived may be used to correct the data to remove the effects of such motion.

As planar gamma ray detector 14 (FIG. 1) steps from one position to the next position, the adjacent view 24, although different, is still quite similar in its brightness pattern to the one which precedes it. The similarity is great enough that it is possible to use cross-correlation techniques between adjacent views 24 to detect the presence of motion between the two views 24, and to determine the magnitude of such motion.

Referring to FIG. 3A, a simplified brightness pattern of a succession of pixels in a column of view N is represented with brightnesses being limited to a maximum of four levels. The second and seventh pixels have a brightness of 2, the fourth pixel has a brightness of 4 and all of the remaining pixels have a brightness of one. An actual image has many more pixels and many more brightness levels.

Referring now also to FIG. 3B, a corresponding brightness pattern in view N+1 is shown in which no image shift has occurred. It will be noted that the pattern of brightness and darkness in FIG. 3B is similar, but not identical, to the pattern in FIG. 3A. That is, the peaks occur in corresponding pixels.

The problem, and a suggestion of its solution, is illustrated in FIG. 3C showing view N+1 in which the data has been shifted two pixels toward the right. In the shifted pattern, the peak in pixel 6, for example, is misplaced. Assume that these one-dimensional arrays represent the arrays of values that are obtained when projection view images are summed in the X direction. Then, the abscissa dimension "pixel" in FIGS. 3A-3C correspond to the Y dimension described previously. As discussed in the sinogram description, the data which is used to reconstruct one particular transaxial slice is obtained from the same Y row in all of the view images. If the data in FIG. 3A represents the correct Y position, then that of FIG. 3C represents data from an image in which the imaged object has shifted in the Y direction relative to the correct location. If transaxial slice reconstruction is attempted using such motion-shifted data, the data selected from FIG. 3C will be incorrect for that particular slice of the body. Instead, data from another slice will be selected.

The suggestion for a solution comes from the fact that, although the pattern in FIG. 3C is shifted two pixels to the right, its shape is nevertheless quite similar to the shape of the pattern in the preceding image in FIG. 3A. I use this shape similarity to discover how far the pattern in FIG. 3C must be shifted to find the best match with the pattern in FIG. 3A. The amount of shift thus detected can then be applied to the digitally stored data to align the images which correspond to shifted data from FIG. 3C with those corresponding to the data from FIG. 3A, as though the shift had not occurred. This removes the artifacts of motion from transaxial slice images reconstructed from this data.

Continuing with the description, if positions of all of the pixels in FIG. 3C are shifted several pixels to the right or left and the brightness value of each pixel in the shifted pattern of FIG. 3C is multiplied by the brightness value of each corresponding pixel in FIG. 3A, and the products of all the multiplications are summed, the sum gives a measure of similarity between the two patterns. When the applied shift is such that the patterns match most closely, a maximum is found in the sum. This corresponds to moving the shifted pattern of FIG. 3C into the position occupied by the unshifted pattern of FIG. 3B.

Referring now also to FIG. 4, the sums of the products for the simplified patterns of FIGS. 3A and 3C are shown for shifts from −3 to +3 pixels. It will be noted that the sum found with a shift of −2 pixels is substantially higher than all other sums. This should be expected since the pattern in FIG. 3C is shifted two pixels in the positive (right) direction. The peak at a shift of −2 may be used both to indicate the presence of interview motion and to provide data for automatic correction of the data to shift out the motion and restore the image quality which would have been obtainable if no motion had taken place.

The brightness patterns in FIGS. 3A-3C are much simpler than an actual image. In addition, the simplified description ignores the possibility of motion in two dimensions.

Referring now to FIG. 5, the process for the more complex real-world image is shown. The simplification afforded by limiting the dimensions of view 24 to 8 by 8 pixels is retained for the following description. The brightness values of all pixels in each row 26 of view N are summed to produce a one-dimensional X summation array 32. A similar operation is performed on each row 26 of view N+1. The two X summation arrays 32 are shifted, then multiplied together, pixel by pixel, in a Y correlator 34, in the manner described in connection with FIGS. 3A-3C to detect the occurrence of a peak. The shift at which such a peak is detected indicates the amount of motion along the Y axis occurring between views N and N+1. A Y-shift signal containing this information is output on a line 36. Besides its usefulness in indicating the presence of motion, the signal on line 36 may also be used in aligning corresponding pixels along the Y axis in views N and N+1 as though no motion had taken place. Similarly, the brightness values in each column 28 of view 24 of views N and N+1 are summed to produce two Y summation arrays 38 which are shifted, multiplied and summed in an X correlator 40 to produce a signal on a line 42 indicating the amount of motion along the X axis between views N and N+1.

The maximum number of pixels over which shifting is attempted may vary with different applications. The smaller the number of pixels over which the search for a peak is undertaken, the faster the processing. With a pixel size of about one-half centimeter, I have discovered that motion exceeding about 10 pixels (about 2 inches) very seldom occurs. However, should it occur, it is so gross that imaging is probably better restarted. Thus, for concreteness of description, and without intending that it be limiting, I employ a shift of from −10 to +10 pixels in my correlation technique.

The actual motion between views is unlikely to equal an integral number of pixels. That is, the shift may be, for example, 2.7 pixels along the X axis and 5.3 pixels along the Y axis. I have discovered that detecting motion down to a fraction of a pixel is valuable in establishing the exact amount of shift to apply to a view.

Referring now to FIG. 6, a correlation histogram is shown in which the largest correlation value 44, shown with horizontal hatching, is flanked on either side by adjacent correlation values 46, indicated by diagonal hatching. I employ a fitted curve 48 to largest correlation value 44 and adjacent correlation values 46 whose peak 50 indicates the position of the shift yielding the maximum correlation value.

Referring now to FIG. 7, there is shown, generally at 52 an imaging system employing the techniques described above. An imaging system 52 includes an image data collection device 54 such as, for example, a planar gamma ray detector 14 (FIG. 1) scanned step-wise about a patient (not shown) to collect an N by M array of data points at each scanning position to produce a view image. An X-Y shift calculator 56, which may operate in the manner indicated in FIGS. 2-6, produces X and Y shift signals for application to a shift module 58. Although other techniques may be employed, in the preferred embodiment, the N+1th view data is shifted in the manner described to align it with the Nth view. Thus, after the second view, the Nth view may itself be a shifted view. As each view is processed, it is thus aligned with all previous views from first to next-to-last.

The corrected data thus produced is transmitted to a storage or display module 60 for the functions noted.

It is not necessary that the functions indicated in FIG. 7, or the previously described correction functions be calculated during data collection. Instead, and this is the preferred embodiment, the data from all views is collected and stored. The shifting is performed off-line. There may be several advantages, not of interest to the present invention, for storing permanently the original unshifted data. The present invention does not preclude such permanent storage and the derivation of motion-corrected image data therefrom.

When images are collected over a 360-degree arc, the sum of all image-to-image shifts should equal zero. Errors may occur in the calculation of shift values making the sum of displacements differ from zero. The displacements calculated in X-Y shift calculator 56 may be totalled for all images about the 360-degree arc and any departure from zero stored as an error value. The error value may then be employed in storage or display module to derive a bias shift applied to the data from all views after the first view. The first view remains unshifted and the data from the remaining views is shifted according to the result of the calculation in X-Y shift calculator 56 plus or minus the bias shift.

The foregoing techniques employ the relatively noisy data in a view for comparison with data in the preceding view for determining the amount of correction required. I have discovered that an improvement in image correction is attainable by operating on the collected data in a four-step process which permits using the entire data set collected in the full scan for providing sets of substantially noise-free images upon which the motion-detection techniques, optionally coupled with motion-correction techniques, may be performed.

Rather than correcting for patient motion on each view as previously described, the improved technique employs the entire original data set to produce, by back projection, transaxial slice reconstruction and reprojection, one reference view related to each view whose motion is to be corrected. Weighting techniques may be employed during such processing to simulate the effects of attenuation. Since each reference view includes contributions from the entire data set rather than from a single view, noise in the reference view is substantially reduced.

The motion-correction operation compares the present view with its appropriate reference view for determining the amount of correcting motion required. That is, if view N is operated on for determining a required shift, the reference view corresponding to view N is employed for the comparison. Since reference view N is substantially noise free, and effects of attenuation may have been accounted for in its processing, the effect of noise or attenuation on the shift determination is substantially reduced. The final stored data may be displayed in the manner described.

The above improved technique operates on the same data base of collected views as the first-disclosed technique. The difference is found in the additional processing steps preceding the correction operation. As before, the raw collected data set may be retained for further use. Indeed, it is contemplated that a single data set may be employed for either or both techniques without requiring the further presence of a patient.

In some imaging situations, the desired information may be accompanied by a large amount of background information which is constant, or slowly varying, spatially. It may be useful to estimate such background component of the signal and to subtract the estimate from the image data before the calculations and displacements of FIG. 7 are performed.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

The invention claimed is:

1. Apparatus for correcting for inter-view motion in an imaging system, comprising: means for collecting first and second views of an object;
   said first and second views being taken from first and second different angles;
   each of said first and second views including at least one of M rows and N columns of image brightness data;
   means for comparing a first pattern of said image brightness data from said first view with a corresponding second pattern of said image brightness data from said second view to produce a coefficient containing information about a similarity therebetween;
   said means for comparing including means for applying a shift to one of said first and second patterns to a plurality of positions for producing a plurality of said coefficients, one at each of said plurality of positions;
   means related to said plurality of coefficients for determining a value of said shift yielding a maximum of said similarity;
   said means for comparing includes:
   first means for summing a brightness of each pixel in one of each row and each column in said first view to produce a first one-dimensional summation array;
   second means for summing a brightness of each pixel in one of each row and each column in said second view to produce a second one-dimensional summation array;
   means for multiplying brightness values of corresponding elements in said first and second one-dimensional summation arrays to produce a plurality of products; and
   means for summing said plurality of products to produce said coefficient.

2. Apparatus according to claim 1, further comprising means responsive to said value of said shift for shifting one of said first and second views an amount related to said value of said shift.

3. Apparatus according to claim 1 wherein said means for determining a value of said shift includes means for fitting a curve to a plurality of said coefficients, a peak of said curve being said value.

4. Apparatus according to claim 3 wherein said plurality of said coefficients includes a maximum one of said coefficients and first and second coefficients adjacent to said maximum.

5. A method for correcting for inter-view motion in an imaging system, comprising: collecting first and second views of an object from first and second different angles, respectively;
   each of said first and second views including at least one of M rows and N columns of image brightness data;
   comparing a first pattern of said image brightness data from said first view with a corresponding second pattern of said image brightness data from said second view to produce a coefficient containing information about a similarity therebetween;
   the step of comparing including applying a shift on one of said first and second patterns to a plurality of positions for producing a plurality of said coefficients, one at each of said plurality of positions;
   determining, based on said plurality of coefficients, a value of said shift yielding a maximum of said similarity;
   the step of comparing includes:
   summing a brightness of each pixel in one of each row and each column in said first view to produce a first one-dimensional summation array;
   summing a brightness of each pixel in one of each row and each column in said second view to produce a second one-dimensional summation array;
   multiplying brightness values of corresponding elements in said first and second one-dimensional summation arrays to produce a plurality of products; and
   summing said plurality of products to produce said coefficient.

6. A method according to claim 5 further comprising shifting one of said first and second views an amount related to said value of said shift.

7. A method according to claim 5 wherein the step of determining a value of said shift includes fitting a curve to a plurality of said coefficients, a peak of said curve being said value.

8. A method according to claim 7 wherein said plurality of said coefficients includes a maximum one of said coefficients and first and second coefficients adjacent to said maximum.

9. Apparatus for correcting for inter-view motion in an imaging system:
- means for collecting and storing a plurality of original views of an object taken in a circle about said object;
- each of said original views including M rows and N columns of image brightness data;
- means for back projecting said plurality of original views to produce a three-dimensional dataset therefrom representing said object;
- means for reprojecting said three-dimensional dataset to produce a plurality of reference views;
- each of said reference views including M rows and N columns corresponding to said original views;
- each of said original views having a corresponding reference view;
- means for comparing a first pattern of said image brightness from a first original view with a second pattern of said image brightness from its reference view to produce a coefficient containing information about similarity therebetween;
- said means for comparing including means for applying a shift to said first pattern to a plurality of positions for producing a plurality of said coefficients, one at each of said plurality of positions; and
- means related to said plurality of coefficients for determining a value of said shift yielding a maximum of said similarity.

10. A method for correcting for inter-view motion in an imaging system:
- collecting and storing a plurality of original views of an object taken in a circle about said object;
- each of said original views including M rows and N columns of image brightness data;
- back projecting said plurality of original views to produce a three-dimensional dataset therefrom representing said object;
- reprojecting said three-dimensional dataset to produce a plurality of reference views;
- each of said reference views including M rows and N columns corresponding to said original views;
- each of said original views having a corresponding reference view;
- comparing a first pattern of said image brightness from an original view with a second pattern of said image brightness from its reference view to produce a coefficient containing information about similarity therebetween;
- applying a shift to said first pattern to a plurality of positions for producing a plurality of said coefficients, one at each of said plurality of positions; and
- determining from said plurality of coefficients a value of said shift indicating a maximum of said similarity.

* * * * *